(12) United States Patent
Ehlis

(10) Patent No.: US 7,179,924 B2
(45) Date of Patent: Feb. 20, 2007

(54) USE OF BENZOTRIAZOLE UV ABSORBERS

(75) Inventor: Thomas Ehlis, Freiburg (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 37 days.

(21) Appl. No.: 11/046,913

(22) Filed: Jan. 31, 2005

(65) Prior Publication Data

US 2005/0158255 A1 Jul. 21, 2005

Related U.S. Application Data

(62) Division of application No. 10/130,235, filed as application No. PCT/EP00/10969 on Nov. 7, 2000, now Pat. No. 7,066,184.

(30) Foreign Application Priority Data

Nov. 16, 1999 (EP) .................................. 99811053

(51) Int. Cl.
C07D 249/04 (2006.01)

(52) U.S. Cl. .......................... 548/255; 548/360; 8/570; 8/573

(58) Field of Classification Search .................... 8/570, 8/573; 548/255, 257, 260
See application file for complete search history.

(56) References Cited

U.S. PATENT DOCUMENTS

| | | | |
|---|---|---|---|
| 3,629,192 A | 12/1971 | Heller et al. ................ | 260/45.8 |
| 4,785,063 A | 11/1988 | Slongo et al. .............. | 526/259 |
| 4,937,349 A | 6/1990 | Burdeska et al. .......... | 548/260 |
| 5,589,529 A | 12/1996 | Reinehr et al. ............ | 524/91 |

FOREIGN PATENT DOCUMENTS

| | | |
|---|---|---|
| DE | 2216578 | 10/1972 |
| EP | 0133164 | 2/1985 |
| EP | 0314620 | 5/1989 |
| EP | 0669330 | 8/1995 |
| GB | 1169859 | 11/1969 |
| GB | 1382861 | 2/1975 |
| GB | 2319035 | 5/1998 |
| JP | 50121178 | 9/1975 |
| JP | 2000141874 A | * 5/2000 |
| SE | 408033 | 2/1966 |
| WO | 92/14717 | 9/1992 |

OTHER PUBLICATIONS

English Abstract of the Japanese patent No. 2000141874 A.*
STN Search Report (Apr. 24, 2006).*

* cited by examiner

Primary Examiner—Eisa Elhilo
(74) Attorney, Agent, or Firm—Kevin T. Mansfield; Mervin G. Wood

(57) ABSTRACT

The use of benzotriazole UV absorbers of formula

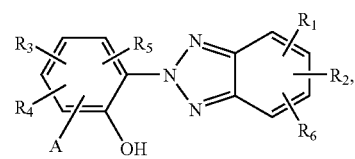
(1)

wherein
A is a radical of formula

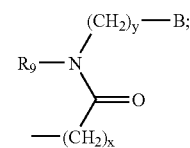
(1a)

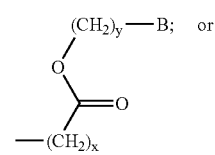

(1b)

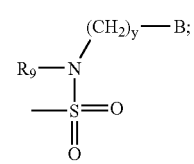

(1c)

B is a radical of formula

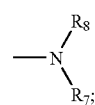
(1d)

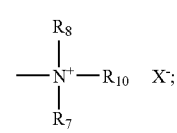

(1e)

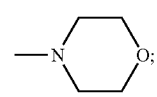

(1f)

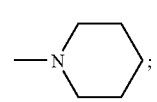

(1g)

-continued

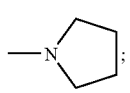 (1h)

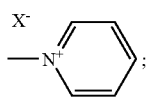 (1i)

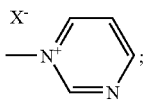 (1k)

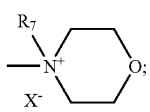 (1l)

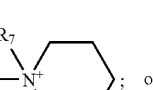 (1m) ; or

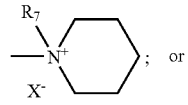 (1n)

$R_1$, $R_2$, $R_3$, $R_4$, $R_5$ and $R_6$ are each independently of the others hydrogen, $C_1$–$C_{16}$ alkyl; $C_5$–$C_7$cycloalkyl; halogen;

$R_9$ is hydrogen, $C_1$–$C_{12}$alkyl; or $C_5$–$C_7$cycloalkyl;
$R_7$, $R_8$ and $R_{10}$ are each independently of the others hydrogen, $C_1$$C_{12}$alkyl, $C_5$–$C_7$cycloalkyl, $C_1$–$C_{12}$hydroxyalkyl;
X is halogen; a radical of formula (1s)

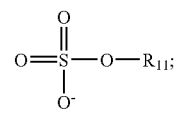 (1s)

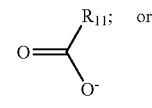 (1t)

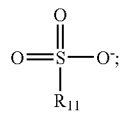 (1u)

sulfate, phosphate, lactate, citrate, tartrate;
$R_{11}$ is $C_1$–$C_{12}$alkyl; or $C_5$–$C_7$cycloalkyl;
$R_{12}$ and $R_{13}$ are each independently of the other hydrogen; or $C_1$–$C_5$alkyl;
x is from 0 to 10; and
y is from 1 to 20;
in the cosmetic treatment of human hair for protection against UV radiation is described.

1 Claim, No Drawings

USE OF BENZOTRIAZOLE UV ABSORBERS

This application is a divisional of application No. 10/130,235, filed Sep. 24,2002 now U.S. Pat. Ser. No. 7,066,184 which is the National Stage of International Application PCT/EP00/10969/, filed Nov. 7, 2000.

The present invention relates to the use of selected uncharged and cationic benzotriazole UV absorbers in the cosmetic treatment of human hair for protection against UV radiation.

When human hair is exposed to sunlight over a prolonged period, various forms of damage may occur. Hair that has been coloured with dyes may undergo changes in colour and shade under the action of sunlight. Blonde hair becomes yellowish. The surface of the hair becomes rougher and at the same time drier. In addition, in time the hair loses its shine.

The use of UV absorbers can effectively protect natural and dyed hair from the damaging rays of the sun. Unfortunately, however, the UV absorbers used hitherto have insufficient affinity for human hair, that is to say they are easily washed out and therefore have only a short-term effect.

It has now been found, surprisingly, that certain uncharged and cationic benzotriazole UV absorbers exhibit very good substantivity in respect of human hair and at the same time provide effective UV protection for the hair.

The uncharged and cationic benzotriazole UV absorbers used according to the invention correspond to formula

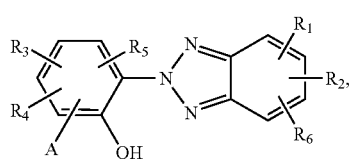

(1)

wherein

A is a radical of formula

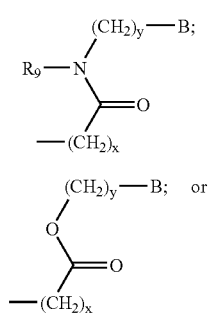

(1a)

(1b)

B is a radical of formula

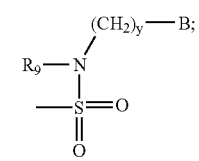

(1c)

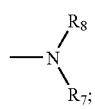

(1d)

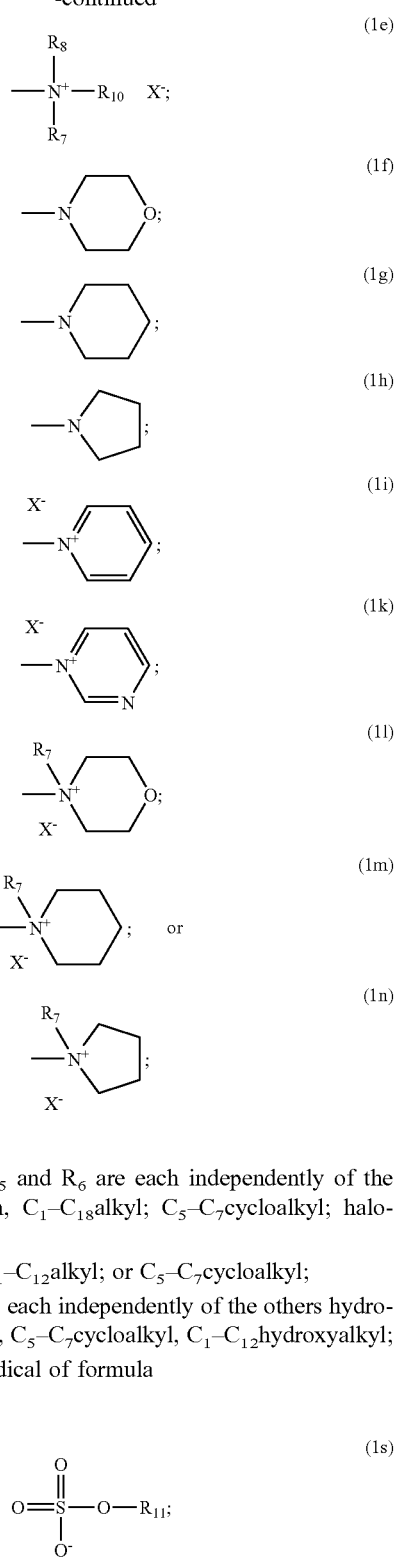

$R_1$, $R_2$, $R_3$, $R_4$, $R_5$ and $R_6$ are each independently of the others hydrogen, $C_1$–$C_{18}$alkyl; $C_5$–$C_7$cycloalkyl; halogen;

$R_9$ is hydrogen, $C_1$–$C_{12}$alkyl; or $C_5$–$C_7$cycloalkyl;

$R_7$, $R_8$ and $R_{10}$ are each independently of the others hydrogen, $C_1$$C_{12}$alkyl, $C_5$–$C_7$cycloalkyl, $C_1$–$C_{12}$hydroxyalkyl;

X is halogen; a radical of formula

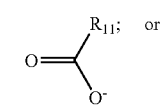

-continued

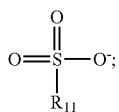
(1u)

sulfate, phosphate, lactate, citrate, tartrate;

$R_{11}$ is $C_1$–$C_{12}$alkyl; or $C_5$–$C_7$cycloalkyl;

$R_{12}$ and $R_{13}$ are each independently of the other hydrogen; or $C_1$–$C_5$alkyl;

x is from 0 to 10; and y is from 1 to 20.

$C_1$–$C_{16}$Alkyl denotes straight-chain and branched hydrocarbon radicals, e.g. methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl; dodecyl; tridecyl; tetradecyl; pentadecyl or hexadecyl.

$C_5$–$C_7$Cycloalkyl is e.g. cyclopentyl, cycloheptyl and especially cyclohexyl.

Halogen is fluorine, bromine, iodine and especially chlorine.

The invention preferably relates to the use of the compounds of formulae

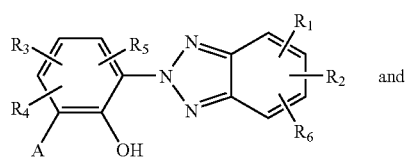
(2)

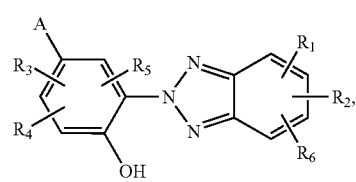
(3)

wherein $R_1$, $R_2$, $R_3$, $R_4$, $R_5$, $R_6$ and A are as defined for formula (1).

According to the invention there are preferably used compounds of formulae (1), (2) and (3) wherein A is a radical of formula

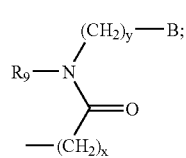
(1a)

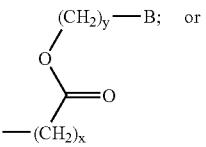
(1b)

(1c)

wherein

B is a radical of formula (1d); or (1e);

X is halogen; or a radical of formula (1s), (1t) or (1u); and x and y are as defined for formula (1).

Special preference is given to compounds of formulae (1), (2) and (3) wherein $R_9$ is hydrogen; or $C_1$–$C_5$alkyl.

The following benzotriazole UV absorbers used according to the invention may be mentioned by way of example:

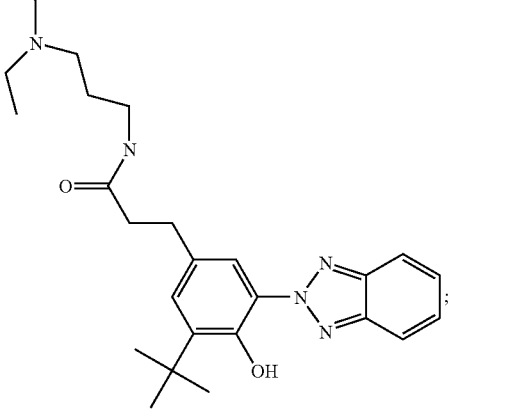
(4)

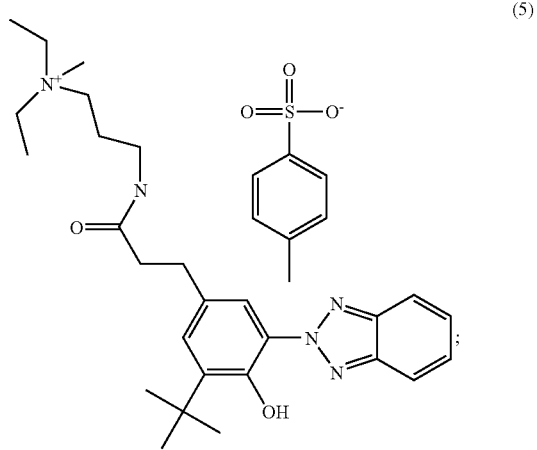
(5)

(6)
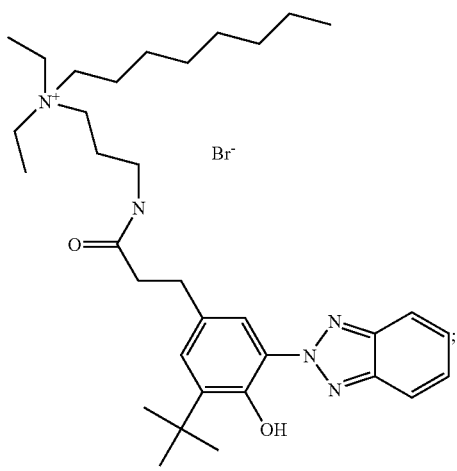
(7)
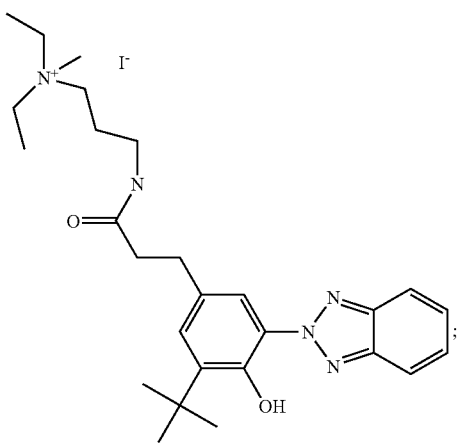
(8)
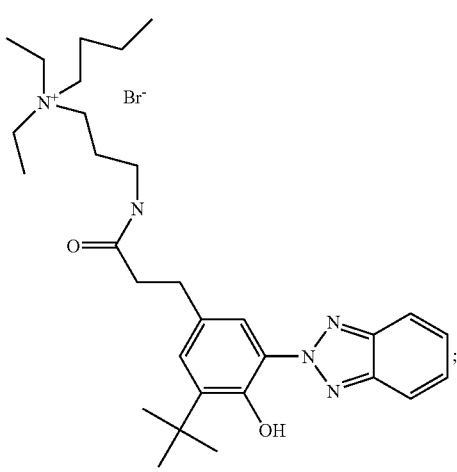
(9)
(10)
(11)
(12)
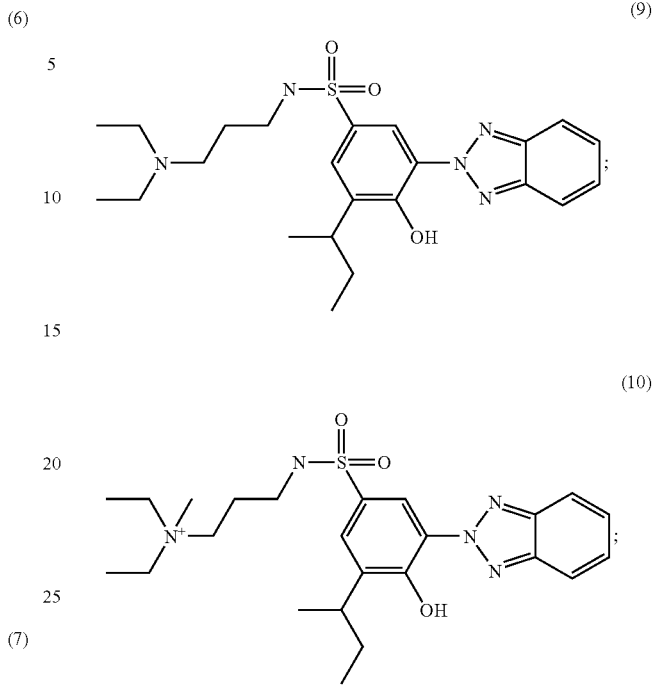
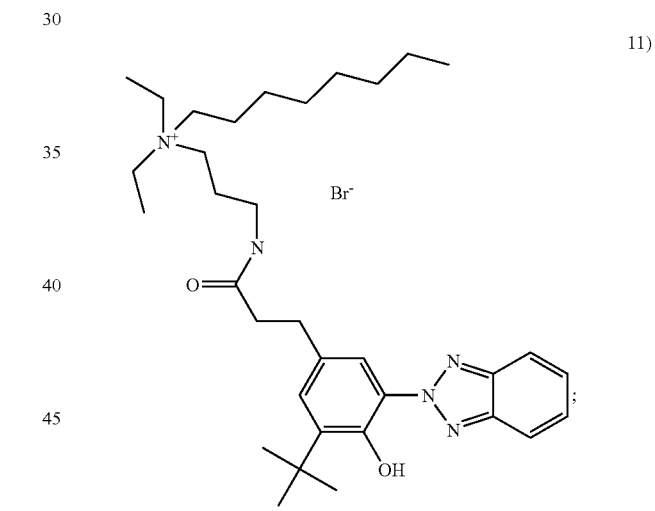
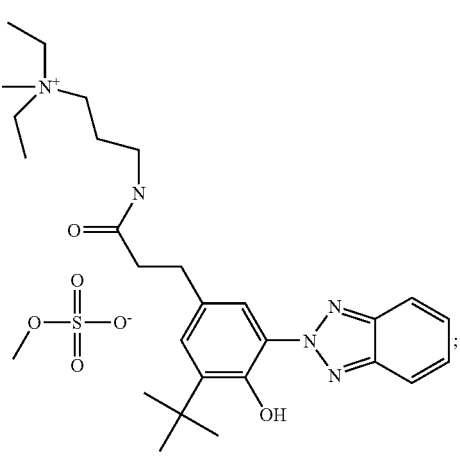

-continued

(13)
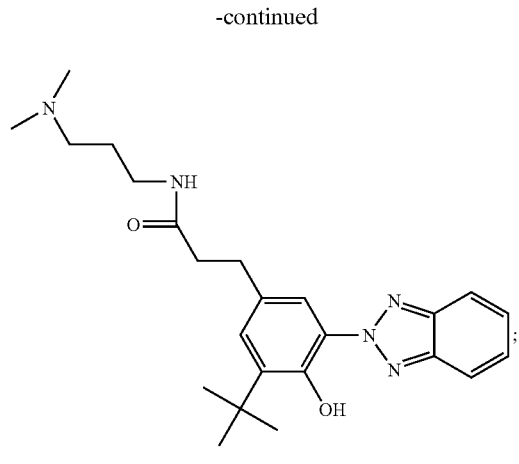

(14)
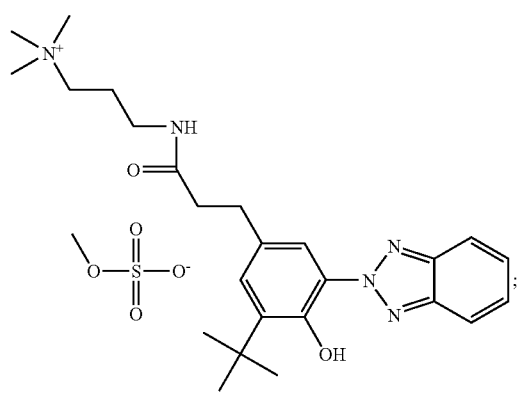

(15)
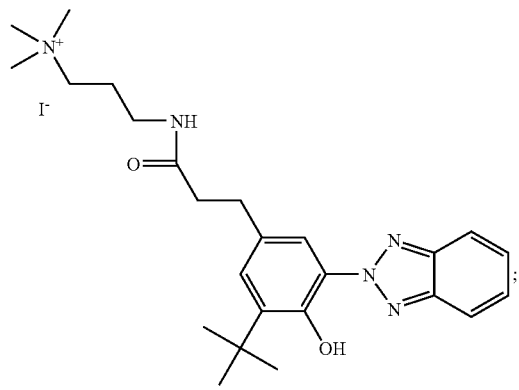

(16)
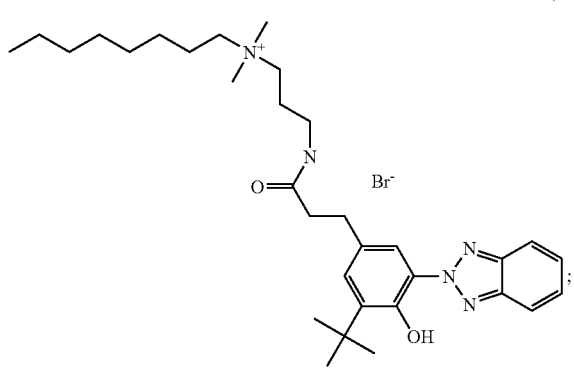

-continued
and

(17)
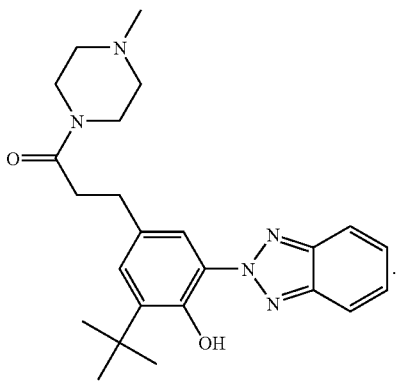

The compounds of formulae (4) to (17) are novel.

The preparation of the benzotriazole compounds of formula (1) used according to the invention when A is a radical of formula (1a) or (1b) is generally carried out by reaction of an acid chloride of formula

(18)
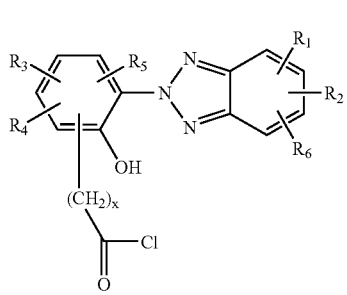

with the corresponding amine of formula (1'a)
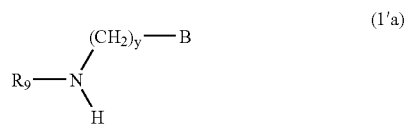

or an alcohol compound of formula (1'b) H—O—$(CH_2)_y$—B, respectively, and optionally subsequent quaternisation (alkylation at the nitrogen atom).

The preparation of the benzotriazole UV absorbers of formula (1) when A is a radical of formula (1c) is generally carried out by reaction of a compound of formula

(19)
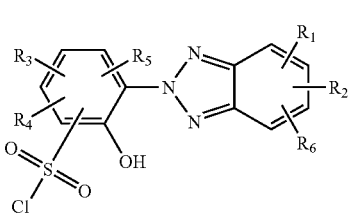

with the corresponding amine of formula

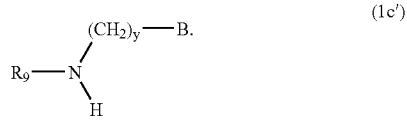

(1c')

Suitable alkylating agents (quaternising agents) are, for example, alkyl halides (chloro- or bromo-alkanes), aliphatic and aromatic sulfonic acid esters, toluenesulfonic acid, benzene-sulfonic acid, sulfuric acid diesters, and also the alkylating reagents mentioned in Houben-Weyl (Houben-Weyl: Methoden der organischen Chemie, G. Thieme Verlag, Stuttgart, New York, 1958, Vol. XI/2. pages 591–640; Houben-Weyl, Methoden der organischen Chemie, G. Thieme Verlag, Stuttgart, New York, 1990, Vol. E16a, pages 997–1032).

Solvents that come into consideration include, for example, alcohols, acetonitrile, ethers, benzonitrile, toluene and benzene. The alkylating agents indicated above can also act as solvents when used in excess.

The reaction temperatures for the quaternisation are from 0 to 200° C., preferably from 5 to 150° C., especially from 20 to 100° C.

The preparation of the benzotriazole compounds of formula (1) according to the invention when A is a radical of formula (1a) or (1b) can also be carried out starting from esters of formula

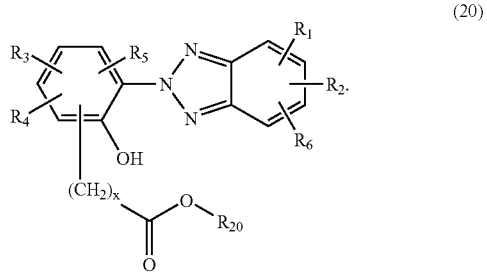

(20)

In that case it is preferable for an alkyl ester (e.g. $R_{20}$=methyl, ethyl, propyl, butyl, isopropyl, tert-butyl) to be reacted with the corresponding amine of formula

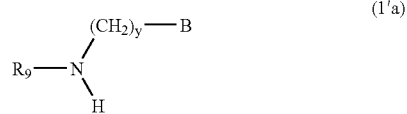

(1'a)

or an alcohol compound of formula (1'b) H—O—$(CH_2)_y$—B, respectively, and optionally subsequently quaternised (alkylation at the nitrogen atom).

The transesterification or amidation can be carried out in the customary organic solvents, but direct reaction of the ester of the general formula (20) with an excess of the amine component or the alcohol component, without the addition of a further solvent, is especially advantageous. The molar ratio of ester of formula (20) to amine or alcohol component is at least 0.9:1. In order to obtain a homogeneous reaction mass and a high yield, an excess of the amine or alcohol component is used.

The reaction temperature is from 50 to 350° C., depending upon the amine or alcohol component used. The reaction can be carried out below normal pressure, at elevated pressure or at normal pressure. On being heated to the final temperature, the more readily volatile alcohol formed during the transesterification or amidation escapes and is thus removed from the reaction mixture by distillation. It is advantageous to heat the reaction mixture at elevated temperature for from 0.5 to 50 hours and to distill off the alcohol formed continuously.

The removal of alcohol is accelerated by a vacuum or by passing a stream of inert gas over the mixture.

In the case of low-boiling amine and alcohol components, the component in question is distilled off from the reaction mixture together with the alcohol that is formed. In the case of high-boiling amine and alcohol components, first predominantly alcohol is distilled off and then the excess amine or alcohol component is completely removed in vacuo. The reaction product remains behind in the reactor.

If a quaternised product is desired, the quaternisation can take place on the lines of a "one-pot reaction" in the same reactor without intermediate isolation.

The quaternisation reaction is carried out without a solvent or in organic solvents. The use of a greater than stoichiometric amount of the alkylating agent is advantageous.

When dialkyl sulfates or tosylates are used as alkylating reagents it is especially advantageous to carry out the reaction in a mixture of an organic solvent (e.g. acetone or ethyl methyl ketone) with water. Optimum reaction conditions are established by regulating the pH value (pH 1–10) and the temperature (–15 to 150° C.).

In some cases the finely suspended starting material can also be quaternised directly in water without the addition of an organic solvent (e.g. with dialkyl sulfates or tosylates as alkylating agents; pH 1–10).

It is also possible to use other quaternisation methods mentioned in Houben-Weyl (Houben-Weyl: Methoden der organischen Chemie, G. Thieme Verlag, Stuttgart, New York, 1958, Vol. XI/2, pages 591–640; Houben-Weyl, Methoden der organischen Chemie, G. Thieme Verlag, Stuttgart, New York, 1990, Vol. E16a, pages 997–1032).

The starting compounds of formula (1) are known, for example from U.S. Pat. No. 4,937,349 or Holzforschung (1997), 51 (6), 511–518, and can be prepared in accordance with the methods described therein.

Carboxylic or sulfonic acid chlorides of formulae (9) and (10) can generally be obtained in accordance with the methods described in Houben-Weyl (Houben-Weyl: Methoden der Organischen Chemie, G. Thieme Verlag, Stuttgart, New York 1985, Vol. E11, pages 1067–1073; Houben-Weyl: Methoden der Organischen Chemie, G. Thieme Verlag, Stuttgart, New York 1952, Vol. VIII, pages 463–478; Houben-Weyl: Methoden der Organischen Chemie, G. Thieme Verlag, Stuttgart, New York 1985, Vol. E5, pages 587–615), for example from the corresponding carboxylic or sulfonic acids or salts thereof.

Some of the starting compounds of formula (19) are known compounds. The compound of formula

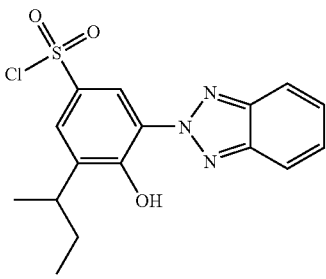
(19')

is novel.

The benzotriazole derivatives of formula (1) according to the invention are broadband UV filters, are distinguished by a high degree of photostability and are readily soluble in polar solvents, including especially cationic surfactants, e.g. Arquads.

They are therefore suitable for the cosmetic treatment of human skin and hair for protection against UV radiation.

The UV absorbers according to the invention are distinguished by
 having a high degree of substantivity with respect to natural and undyed human hair and
 ensuring a high degree of UV protection for natural and dyed hair.

They can therefore be used as light-protective agents in cosmetic, pharmaceutical and veterinary-medicinal preparations, for which, as water-soluble compounds, they are generally used in dissolved form.

The invention therefore relates also to a cosmetic preparation comprising at least one compound of formula (1) as well as cosmetically tolerable carriers or adjuvants.

A cosmetic preparation according to the invention contains especially from 0.25 to 15% by weight, based on the total weight of the composition, of a benzotriazole UV absorber of formula (1).

The hair-cosmetic formulation, in addition to comprising the UV absorber according to the invention, may also comprise one or more further UV-protective substances of the following classes of substance:
1. p-aminobenzoic acid derivatives, e.g. 4-dimethylaminobenzoic acid 2-ethylhexyl ester;
2. salicylic acid derivatives, e.g. salicylic acid 2-ethylhexyl ester;
3. benzophenone derivatives, e.g. 2-hydroxy-4-methoxybenzophenone and the 5-sulfonic acid derivative thereof;
4. dibenzoylmethane derivatives, e.g. 1-(4-tert-butylphenyl)-3-(4-methoxyphenyl)propane-1,3-dione;
5. diphenyl acrylates, e.g. 2-ethylhexyl-2-cyano-3,3-diphenyl acrylate and 3-(benzofuranyl)-2-cyanoacry
6. 3-imidazol-4-yl-acrylic acid and esters;
7. benzofuran derivatives, especially 2-(p-aminophenyl) benzofuran derivatives, described in EP-A-582 189, U.S. Pat. No. 5,338,539, U.S. Pat. No. 5,518,713 and EP-A-613 893;
8. polymeric UV absorbers, e.g. the benzylidene malonate derivatives described in EP-A-709 080;
9. cinnamic acid derivatives, e.g. the 4-methoxycinnamic acid 2-ethylhexyl ester and isoamyl ester or cinnamic acid derivatives disclosed in U.S. Pat. No. 5,601,811 and WO 97/00851;
10. camphor derivatives, e.g. 3-(4'-methyl)benzylidene-bornan-2-one, 3-benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis (7,7dimethyl-2-oxo-bicyclo[2.2.1]heptane-1methanesulfonic acid) and salts, 3-(4'-sulfo)benzylidene-bornan-2-one and salts; camphorbenzalkonium methosulfate,
11. hydroxyphenyltriazine compounds, e.g. 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris (trimethylsilyloxy-silylpropyloxy)-2-hydroxy]-phenyl}-6-(4-methoxyphenyl)-1,3,5triazine; 2,4-bis{[4-(2"-methylpropenyloxy)-2-hydroxy]-phenyl}-6-(4-methoxyphenyl)-1,3,5-triazine; 2,4-bis{[4-(1',1',1',3',5',5',5',-heptamethyltrisilyl-2"-methyl-propyloxy-2hydroxy]-phenyl}-6-(4methoxyphenyl)-1,3,5-triazine; 2,4-bis{[4-(3-(2-propyloxy)-2-hydroxy -propyloxy)-(2-hydroxy]-phenyl}-6-[4-ethylcarboxyl)-phenylamino]-1, 3,5-triazine;
12. benzotriazole compounds, e.g. 2,2'-methylene-bis(6-(2H-benzotriazol-2-yl)-4-(1,1,3,3-tetramethylbutyl)-phenol

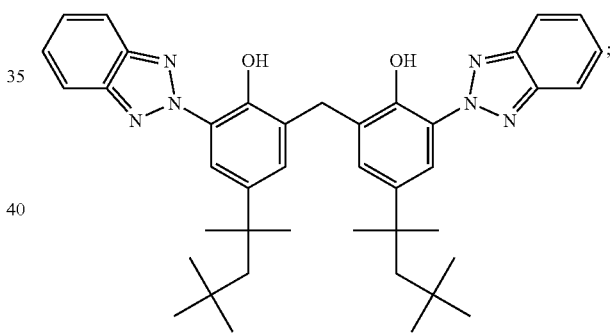

13. trianilino-s-triazine derivatives, e.g. 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
14. 2-phenylbenzimidazole-5-sulfonic acid and salts thereof;
15. menthyl-o-aminobenzoate;
16. $TiO_2$ (variously encapsulated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) can also be used as additional UV-protective substances in the hair formulation according to the invention.

Furthermore, the hair-cosmetic formulation can also be used together with known antioxidants, e.g. vitamin E, carotinoids or HALS compounds, and especially phenolic antioxidants. Examples of phenolic antioxidants that can be used according to the invention are listed in Table 1:

TABLE 1
Compound of formula
(21) 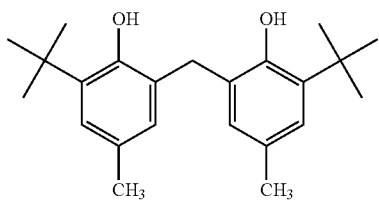
(22) 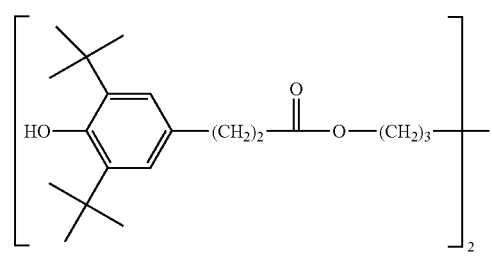
(23) 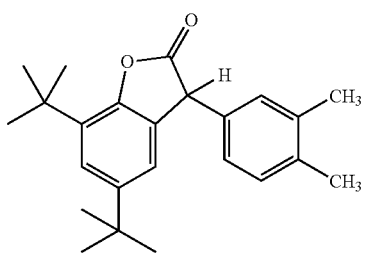
(24) 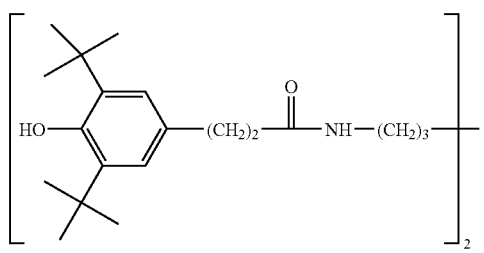
(25) 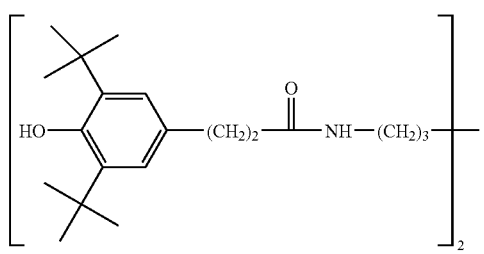
(26) 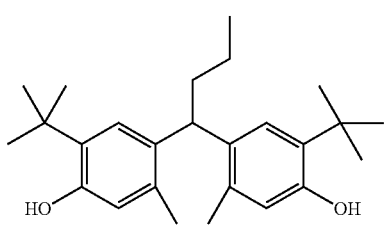

TABLE 1-continued
Compound of formula
(27) 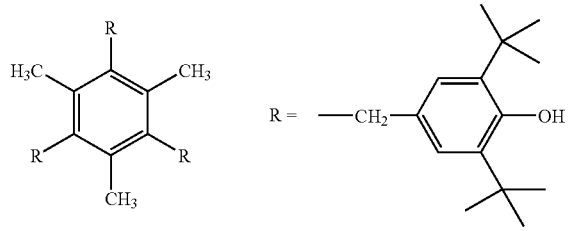
(28) 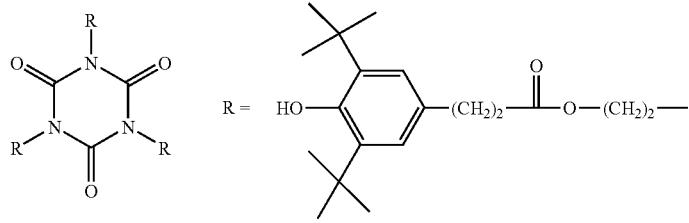
(29) 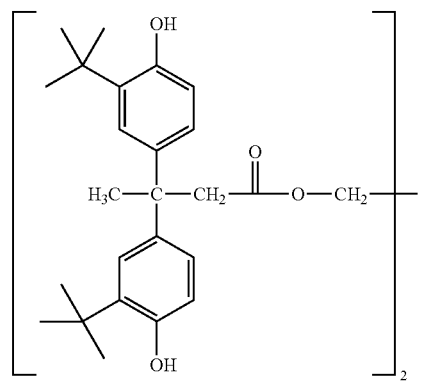
(30) 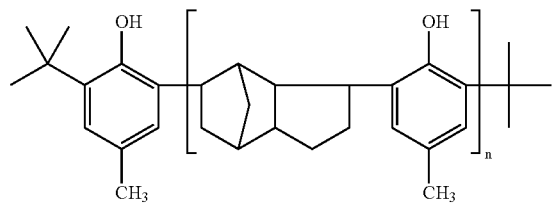
n = 1–3
(31) 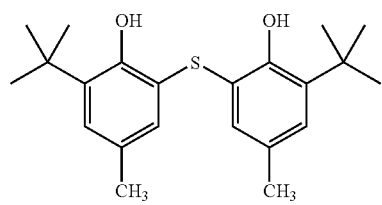

TABLE 1-continued
| Compound of formula | |
|---|---|
| (32) | 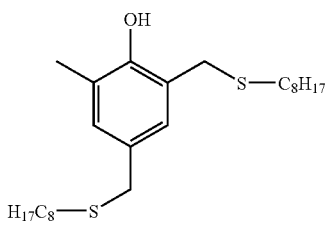 |
| (33) | 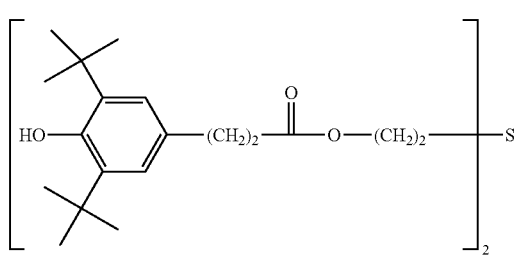 |
| (34) | 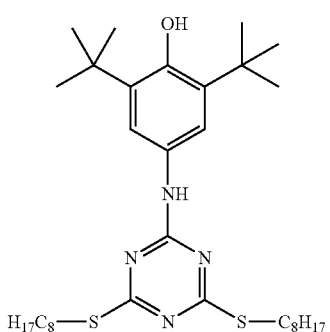 |
| (35) | 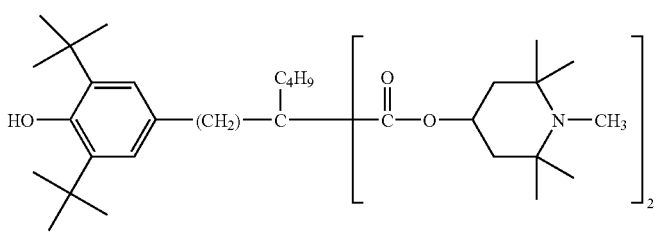 |
| (36) | 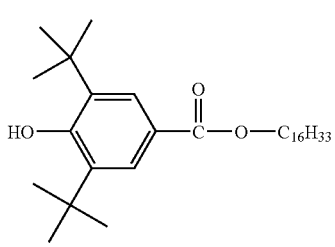 |

TABLE 1-continued
| Compound of formula | |
|---|---|
| (37) | 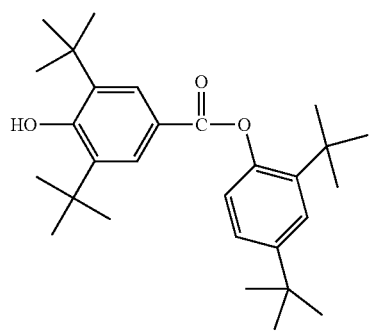 |
| (38) | 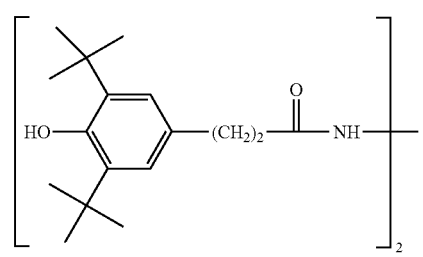 |
| (39) | 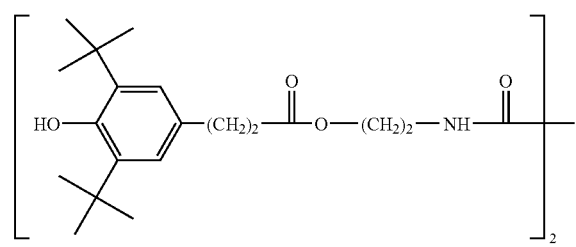 |
| (40) | 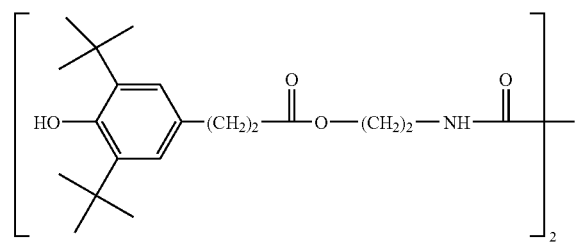 |
| (41) | 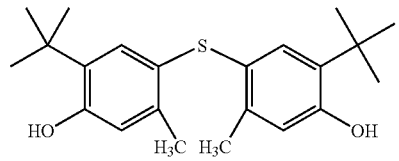 |
| (42) | 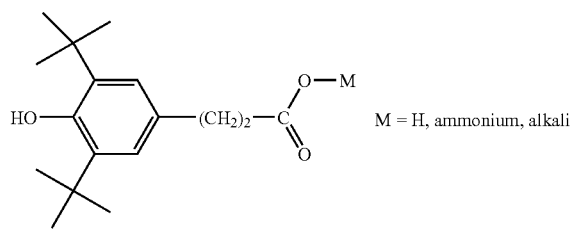 M = H, ammonium, alkali |

TABLE 1-continued
| Compound of formula | |
|---|---|
| (43) | 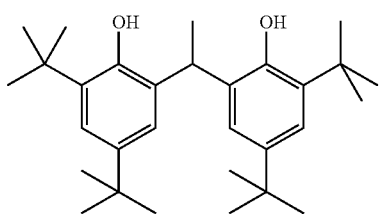 |
| (44) | 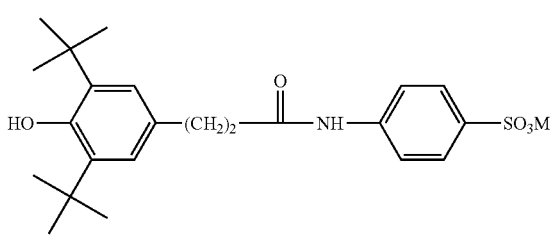
M = H, Na |
| (45) | 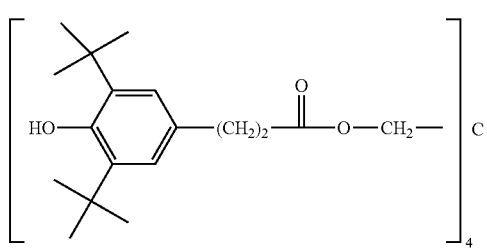 |
| (46) | 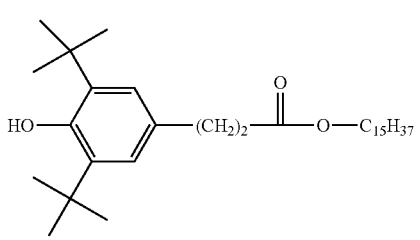 |
| (47) | 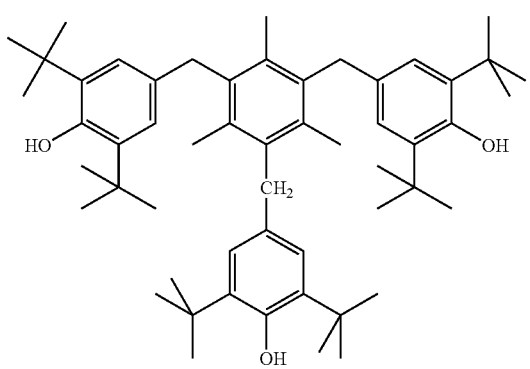 |
| (48) | butylated hydroxytoluene (BHT) |
| (49) | butylated hydroxyanisole (BHA) |
| (50) | gallates, especially propyl gallate |

TABLE 1-continued

Compound of formula

(51)  N-[3-(3,5-di-tert-butyl-4-hydroxyphenyl)propionyl]sulfanilic acid,
5-[3-(3,5-di-tert-butylphenyl)propionamido]-1-naphthalenesulfonic acid

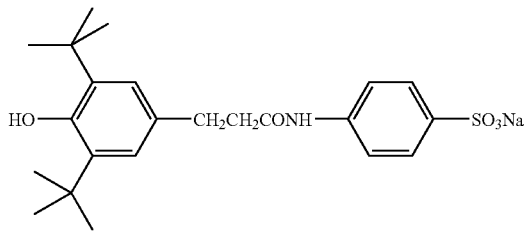

and similar compounds

The cosmetic preparations can be prepared by physically mixing the UV absorber(s) with the adjuvant using customary methods, e.g. by simply stirring the individual components together.

The cosmetic preparation according to the invention may be formulated as a water-in-oil or oil-in-water emulsion, as an oil-in-alcohol lotion, as a vesicular dispersion of an ionic or non-ionic amphiphilic lipid, as a gel, a solid stick or as an aerosol formulation.

In the case of a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

For the preparation of the cosmetic preparations according to the invention it is possible to use any conventially used emulsifier, for example one or more ethoxylated esters of natural derivatives, e.g. polyethoxylated esters of hydrogenated castor oil; or a silicone oil emulsifier, e.g. silicone polyol; a fatty acid soap, which may or may not be ethoxylated; an ethoxylated fatty alcohol; a sorbitan ester, which may or may not be ethoxylated; an ethoxylated fatty acid; or an ethoxylated glyceride.

The cosmetic preparations may also comprise further components, e.g. emollients, emulsion stabilisers, skin humectants, skin-tanning accelerators, thickeners, e.g. xanthane, moisture-retaining agents, e.g. glycerol, preservatives, perfumes and colourings.

Cosmetic formulations according to the invention are contained in a variety of cosmetic preparations. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose and pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks; deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or after-shave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The cosmetic preparations according to the invention are distinguished by excellent protection of human hair against the damaging effect of sunlight over a prolonged period of exposure.

The following hair-cosmetic formulations, for example, may especially be used:

$a_1$) spontaneously emulsifying stock formulation, consisting of the benzotriazole UV absorber according to the invention, PEG-6 $C_{10}$oxoalcohol and sorbitan sesquioleate, to which water and any desired quaternary ammonium compound, e.g. 4% minkamidopropyl dimethyl-2-hydroxyethylammonium chloride or Quaternium 80 is added;

$a_2$) spontaneously emulsifying stock formulation consisting of the benzotriazole UV absorber according to the invention, tributyl citrate and PEG-20 sorbitan monooleate, to which water and any desired quaternary ammonium compound, e.g. 4% minkamidopropyl dimethyl-2-hydroxyethylammonium chloride or Quaternium 80 is added;

b) Quat-doped solutions of the benzotriazole UV absorber according to the invention in butyl triglycol and tributyl citrate;

c) mixtures or solutions of the benzotriazole UV absorber according to the invention with n-alkylpyrrolidone.

The present invention relates also to a method of treating natural and dyed human hair for protection against the damaging effect of UV radiation. The method comprises treating the hair with a shampoo, a lotion, a gel or an emulsion for rinsing, before or after shampooing, before or after colouring or colour-removal, before or after a permanent wave or a destyling operation, with a lotion, a foam or a gel for styling, with a lotion, a foam or a gel for brushing or for waving, with a hair lacquer or with a composition for a permanent wave or for destyling or for colouring or removing colour from the hair, wherein the shampoo, the lotion, the gel, the emulsion, the foam, the hair lacquer or the composition for a permanent wave, for destyling, for colouring or for removing colour comprises at least one benzotriazole compound of formula (1).

The benzotriazole UV absorbers according to the invention are also suitable for stabilising personal care products and household products. The invention relates also to that use.

They are especially suitable for the stabilisation of skin-care preparations, bath and shower additives, perfume- and odorant-containing preparations, hair-care preparations, dental care preparations, preparations having a deodorising and perspiration-inhibiting effect, preparations having a cosmetic effect, light-protective preparations and preparations containing active ingredients.

The non-quaternised compounds of the benzotriazole UV absorbers of formula (1) according to the invention are also suitable as UV absorbers for industrial use, e.g. for plastics, surface-coatings and films, natural or synthetic resins, wax-containing substances or natural rubber.

The benzotriazole UV absorbers of formula (1) according to the invention are also effective light stabilisers for organic materials, for example for a large number of polymers. The use of compounds of formula (1) for applications in colour-photographic material or in surface-coatings is especially advantageous. The stabilisers according to the invention or mixtures thereof are preferably used in an amount of from 0.1 to 5% by weight, especially from 0.5 to 3% by weight, based on the organic material. Suitable polymers are listed, for example, in EP-A-0 057 160.

The benzotriazole UV absorbers of formula (1) according to the invention are also suitable for the photochemical stabilisation of natural and dyed or printed fibre materials, for example of silk, leather, wool, polyamide or polyurethanes, and especially of all kinds of cellulosic fibre materials. Such fibre materials include, for example, natural cellulose fibres, such as cotton, linen, jute and hemp, and also cellulose and regenerated cellulose. Textile fibre materials of cotton are preferred.

The compounds of formula (1) are also suitable for the photochemical stabilisation of hydroxyl-group-containing fibres that are present in blend fabrics, for example mixtures of cotton with polyester fibres or polyamide fibres.

A further preferred field of use relates to the blocking or reduction of the UV radiation passing through the said textile materials (UV cutting) and to the increased sun protection offered to human skin by the textile materials treated with the benzotriazole UV absorbers according to the invention.

For that purpose, one or more different compounds of formula (1) are advantageously applied to the textile fibre material in an amount of from 0.01 to 5% by weight, preferably from 0.1 to 3% by weight, and especially from 0.25 to 2% by weight, based on the weight of the fibre material, in accordance with one of the customary dyeing methods. When the textile fibre material is a dyed cellulosic material, the application of the UV absorber of formula (1) can take place before, during or after dyeing, preferably simultaneously with the application of the dye.

The compounds of formula (1) according to the invention can be applied to the fibre material and fixed to the fibre in a variety of ways, especially in the form of aqueous solutions or print pastes. They have good affinity and are suitable both for the exhaust process and for pad-dyeing; they can be used at low temperatures and require only short steaming times in the pad-steam process. The degrees of fixing are high and unfixed dye can be washed off readily, the difference between the degree of exhaust and the degree of fixing being remarkably small.

The compounds of formula (1) are also suitable for printing, especially on cotton.

The textile fibre materials treated with the compounds of formula (1) according to the invention have enhanced protection against photochemical fibre degradation and yellowing phenomena and in the case of dyed fibre material exhibit enhanced (high temperature) light fastness. Special mention should be made of the greatly improved light-protective action of the treated textile fibre material, especially the good protective action with respect to short-wave UVB rays. This has the effect that a textile fibre material treated with a compound of formula (1) according to the invention has a greatly increased sun protection factor (SPF) in comparison with untreated fabric.

The sun protection factor is defined as the quotient obtained from a damaging dose of UV radiation without sun protection and a damaging dose of UV radiation with sun protection. Accordingly, a sun protection factor is also a measure of the permeability to UV radiation of untreated fibre materials and of fibre materials treated with a compound of formula (1) according to the invention. The determination of the sun protection factor of textile fibre materials is explained, for example, in WO 94/04515 or in J. Soc. Cosmet. Chem. 40, 127–133 (1989) and can be carried out analogously thereto.

Advantageously the compounds according to the invention also have the effect that they do not stain the textile fibre material so treated.

The benzotriazole UV absorbers according to the invention also exhibit a pronounced antimicrobial action, especially against pathogenic gram-positive and gram-negative bacteria and also against bacteria of skin flora, e.g. *Corynebacterium xerosis* (bacteria that cause body odour), and also against yeasts and moulds. They are therefore especially suitable in the disinfection of the skin and mucosa and of integumentary appendages (hair), more especially in the disinfection of the hands and of wounds.

They are therefore suitable as antimicrobial active ingredients and preservatives in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The personal care preparation will comprise from 0.01 to 15% by weight, preferably from 0.1 to 10% by weight, based on the total weight of the composition, of the benzotriazole compound of formula (1), and cosmetically tolerable adjuvants.

An antimicrobial soap has, for example, the following composition:
0.01 to 5% by weight of the compound of formula (1)
0.3 to 1% by weight titanium dioxide
1 to 10% by weight stearic acid and
ad 100% soap base, e.g. the sodium salts of tallow fatty acid and coconut fatty acid or glycerol.

A shampoo has, for example, the following composition:
0.01 to 5% by weight of the compound of formula (1)
12.0% by weight sodium laureth-2-sulfate
4.0% by weight cocamidopropyl betaine
3.0% by weight NaCl and
water ad 100%.

A deodorant has, for example, the following composition:
0.01 to 5% by weight of the compound of formula (1)
60% by weight ethanol
0.3% by weight perfume oil and
water ad 100%.

The invention relates also to an oral composition, comprising
0.01 to 15% by weight, based on the total weight of the composition, of the compound of formula (1), and orally tolerable adjuvants.

Example of an oral composition:
10% by weight sorbitol
10% by weight glycerol
15% by weight ethanol
15% by weight propylene glycol
0.5% by weight sodium lauryl sulfate
0.25% by weight sodium methylcocyl taurate
0.25% by weight polyoxypropylene/polyoxyethylene block copolymer
0.10% by weight peppermint flavouring
0.1 to 0.5% by weight of a compound of formula (1) and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The benzotriazole UV absorbers according to the invention can also be used in the photochemical stabilisation of paper and cardboard, more especially ink-jet paper, photo paper and heat-sensitive recording materials.

They are also suitable as stabilisers for inks in ink-jet printing applications, that is to say as UV protection for the dyes contained in the inks.

The benzotriazole UV absorbers according to the invention are especially suitable for preventing yellowing of paper or pulp, especially when those materials still contain lignin.

The benzotriazole UV absorbers according to the invention are also used in stabilising wooden substrates against damage by light and heat.

The following Examples serve to illustrate the invention but do not limit the invention to the Examples.

PREPARATION EXAMPLES FOR NEW COMPOUNDS

Example 1

Preparation of the Compound of Formula

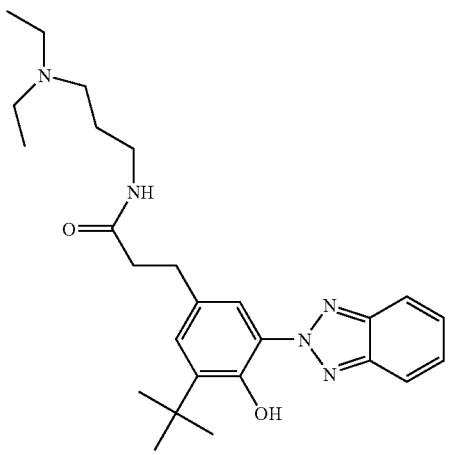

(101)

400 ml of toluene and 76.94 g (0.215 mol) of carboxylic acid chloride of formula

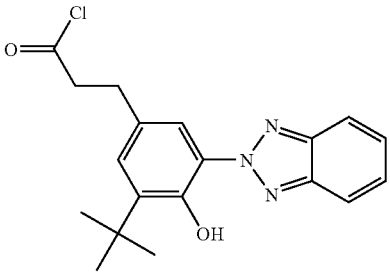

(101a)

(the compound is described in Holzforschung (1997), 51(6), 511–518) are used as initial charge and, at room temperature, first 26.7 g (0.205 mol) of 3-diethylamino-1-propylamine and then 20.75 g (0.205 mol) of triethylamine are added dropwise. The mixture is heated to 80° C. After 5 h, the mixture is filtered while hot through a folded filter; the filtrate is washed twice with water, dried over $Na_2SO_4$ and concentrated in vacuo. The residue, which is initially fluid, crystallises out and is recrystallised from acetone/petroleum ether (very good solubility in acetone).

Yield: 52 g (56%); colourless crystals; m.p.: 89–90° C.
Elementary analysis:

|  | % C | % H | % N |
|---|---|---|---|
| calculated: | 69.15 | 8.26 | 15.51 |
| found: | 68.93 | 8.20 | 15.21 |

NMR Data:
$^{13}C$ NMR (90 MHz, $CDCl_3$): δ=12.09 ($CH_3$), 25.74 ($CH_2$), 29.94 (tert-butyl $CH_3$), 31.94 ($CH_2$), 35.88 (tert-butyl Cq), 39.5 ($CH_2$), 40.46 ($CH_2$), 47.09 ($CH_2N$), 53.08 ($CH_2N$), 117.99 (aryl CH), 119.23 (aryl CH), 125.96 (aryl CH), 127.98 (aryl CH), 128.57 (aryl CH), 132.18 (aryl Cq), 139.81 (aryl Cq), 143.05 (aryl Cq), 147.77 (aryl Cq), 172.09 (C=O).

Example 2

Preparation of the Compound of Formula

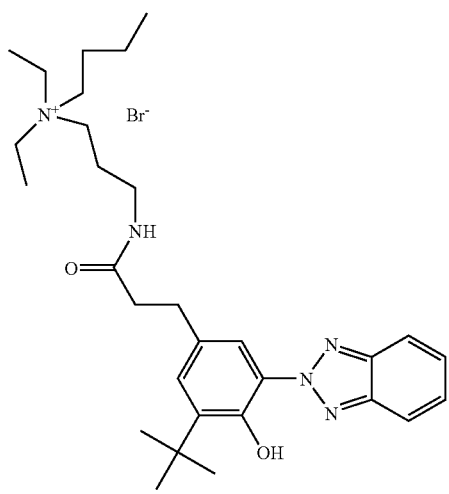

(102)

9 g (0.02 mol) of the compound of formula (101) and 100.3 g of 1-bromobutane (0.725 mol) are mixed together and boiled under reflux (about 100° C.) for 48 hours. After cooling, two liquid phases are formed. The upper, cloudy phase is decanted off. The heavier phase crystallises out after the addition of a small amount of tert-butyl methyl ether. Recrystallisation from chloroform/ethyl acetate and drying at 60° C. in vacuo yields colourless crystals.

Yield: 9.2 g (78%); colourless crystals; m.p.: 105–107° C.

NMR Data:
$^{13}C$ NMR (90 MHz, $CDCl_3$): δ=8.31 ($CH_3$), 13.96 ($CH_3$), 20.06 ($CH_2$), 22.77 ($CH_2$), 24,16 ($CH_2$), 29.92 (tert-butyl $CH_3$), 31.50 ($CH_2$), 35.84 (tert-butyl Cq), 36.22 ($CH_2$), 38.30 ($CH_2$) 54.24 ($CH_3CH_2N$), 57.31 ($CH_2N$), 58.19 ($CH_2N$), 117.88 (aryl CH), 119.29 (aryl CH), 125.68 (aryl Cq), 128.02 (aryl CH), 128.81 (aryl CH), 132.27 (aryl Cq), 139.63 (aryl Cq), 142.92 (aryl Cq), 147.52 (aryl Cq), 173.64 (C=O).

Example 3

Preparation of the Compound of Formula

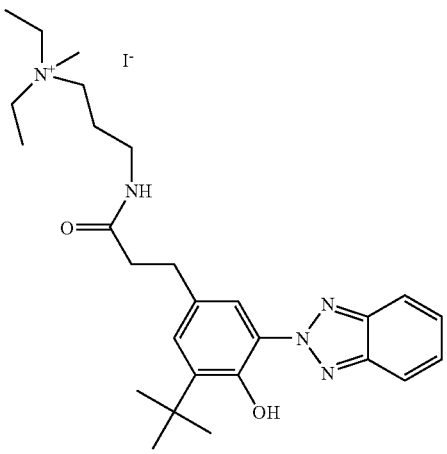

(103)

28 g of ethanol and 6.32 g (0.014 mol) of the compound of formula (101) are mixed together and 13.91 g of methyl iodide (0.098 mol) dissolved in 5 g of ethanol are added dropwise at room temperature. After being heated at 60° C. for 12 hours, the mixture is cooled. The product is precipitated by the addition of hexane (10 ml) and ethanol (2 ml) and dried at 80° C. in vacuo.

Yield: 6.5 g (78%); colourless crystals; m.p.: 205–207° C.

NMR Data:
$^{13}C$ NMR (90 MHz, $[D_6]DMSO$): δ=10.01 ($CH_3CH_2N$), 24.74 ($CH_2$), 31.92 ($CH_2$), 32.99 ($CH_2$), 37.65 (tert-butyl C), 38.06 ($CH_2$), 39.68 ($CH_2$), 49.18 ($CH_3N$), 58.23 ($CH_3CH_2N$), 60.09 ($CH_3CH_2N$), 120.24 (aryl CH), 122.10 (aryl CH), 128.19 (aryl Cq), 130.61 (aryl CH), 130.70 (aryl CH), 134.73 (aryl Cq), 141.14 (aryl Cq), 145.11 (aryl Cq), 149.11 (aryl Cq), 174.14 (C=O).

Example 4

Preparation of the Compound of Formula

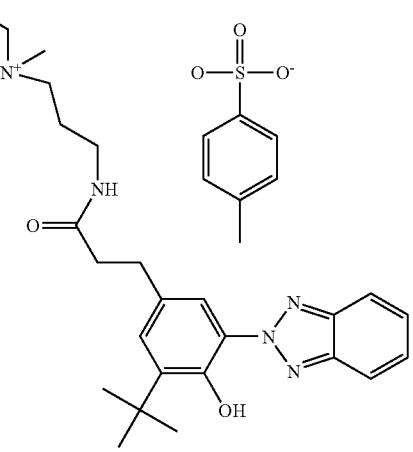

(104)

30 g of ethanol and 5.42 g (0.012 mol) of the compound of formula (101) are mixed together and 12.29 g (0.066 mol) of 4-toluenesulfonic acid methyl ester are added dropwise at room temperature. After being heated at 80° C. for 12 hours, the mixture is cooled. A colourless solid precipitates out from the reaction mixture. The solid is filtered off, washed with tert-butyl methyl ether and dried at 60° C. in vacuo.

Yield: 3 g (39%); colourless crystals; m.p.: 91–93° C.

Example 5

Preparation of the Compound of Formula (105)

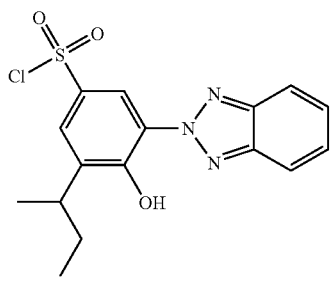

(105)

129 g of the sulfonic acid salt of formula

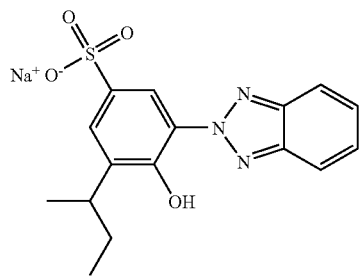

(105a)

(described in U.S. Pat. No. 4,937,349) are suspended in 500 ml of chlorobenzene, and 5 ml of DMF are added. 62.5 g of SOCl$_2$ are slowly introduced dropwise into the mixture at 80–85° C. and stirring is then carried out at 100° C. for 1 h. After cooling, a small amount of kieselguhr is added to the reaction mixture and filtering is carried out. After concentration of the filtrate by evaporation in vacuo there are obtained 136 g of crude sulfonyl chloride which is purified by recrystallisation from cyclohexane/toluene 9:1.

Yield: 102 g (80%); colourless crystals; m.p.: 147–148° C.

NMR Data:

$^{13}$C NMR (90 MHz, CDCl$_3$): δ=10.01 (CH$_3$), 12.73 (CH$_3$), 20.55 (CH$_3$), 30.01 (CH$_2$), 35.09 (CH$_3$), 118.50 (aryl CH), 119.57 (aryl CH), 125.49 (aryl Cq), 126.59 (aryl CH), 129.48 (aryl CH), 136.02 (aryl Cq), 140.55 (aryl Cq), 143.59 (aryl Cq), 153.90 (aryl Cq).

Example 6

Preparation of the Compound of Formula

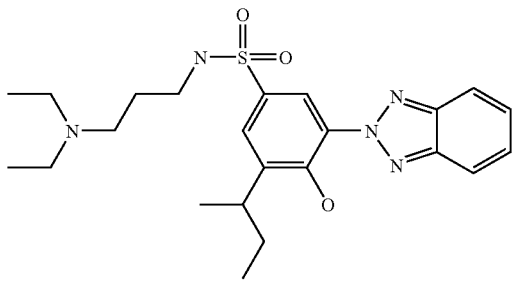

(106)

Analogously to Example 1, equimolar amounts of the sulfonyl chloride of formula (105) are reacted with 3-diethylamino-1-propylamine.

NMR Data:

$^{13}$C NMR (90 MHz, CDCl$_3$): δ=10.51 (CH$_3$CH$_2$N), 11.06 (CH$_3$), 18.96 (CH$_3$), 23.53 (CH$_2$), 28.38 (CH$_2$), 33.20 (CH$_3$CH), 43.49 (CH$_2$N), 45.53 (CH$_3$CH$_2$N), 52.35 (CH$_2$N), 116.64 (aryl CH), 117.41 (aryl CH), 123.66 (aryl Cq), 125.16 (aryl CH), 127.45 (aryl CH), 130.34 (aryl Cq), 137.52 (aryl Cq), 141.75 (aryl Cq), 149.61 (aryl Cq).

Example 7

Preparation of the Compound of Formula

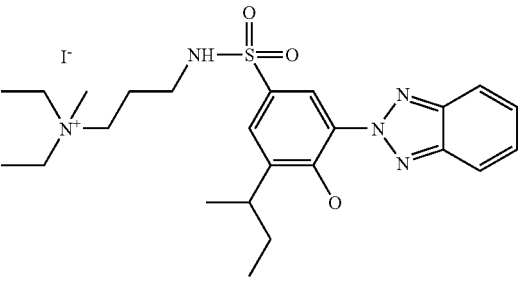

(107)

The alkylation with methyl iodide is carried out analogously to Example 3.

NMR Data:

$^{13}$C NMR (90 MHz, CDCl$_3$): δ=10.51 (CH$_3$CH$_2$N), 11.06 (CH$_3$), 18.96 (CH$_3$ ), 23.53 (CH$_2$), 28.38 (CH$_2$), 33.20 (CH$_3$CH), 43.49 (CH$_2$N), 45.53 (CH$_3$CH$_2$N), 52.35 (CH$_2$ N ), 116.64 (aryl CH), 117.41 (aryl CH), 123.66 (aryl Cq), 125.16 (aryl CH), 127.45 (aryl CH), 130.34 (aryl Cq), 137.52 (aryl Cq), 141.75 (aryl Cq), 149.61 (aryl Cq).

Example 8

Preparation of the Compound of Formula

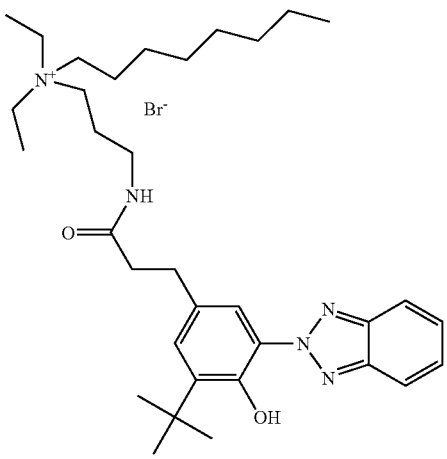

(108)

The amide of formula (101) (0.18 mol) and bromooctane (0.78 mol) are heated at 80° C. for 5 days. The target compound precipitates out after cooling and is filtered off and recrystallised.

Yield: 80%.

NMR Data:

$^{13}$C NMR (90 MHz, CDCl$_3$): δ=8.33 (CH$_3$CH$_2$N), 14.40 (octyl CH$_3$), 22.32 (CH$_2$), 22.79 (CH$_2$), 22.88 (CH$_2$), 26.73 (CH$_2$), 29.07 (CH$_2$), 29.36 (CH$_2$), 29.93 (tert-butyl CH$_3$), 31.53 (CH$_2$), 31.92 (CH$_2$), 32.09 (CH$_2$), 35.84 (tert-butyl Cq), 36.21 (CH$_2$), 38.31 (CH$_2$), 54.24 (CH$_3$CH$_2$N ), 57.35 (CH$_2$N), 58.38 (CH$_2$N), 117.88 (aryl CH), 119.31 (aryl CH), 125.69 (aryl Cq), 128.00 (aryl CH), 128.82 (aryl CH), 132.27 (aryl Cq), 139.61 (aryl Cq), 142.92 (aryl Cq), 147.52 (aryl Cq), 173.65 (C=O).

Example 9

Preparation of the Compound of Formula

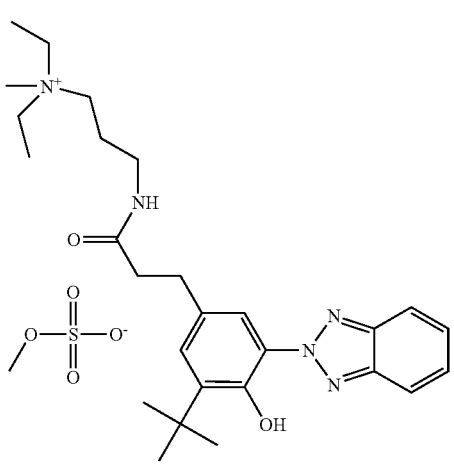

(109)

Amidation

A mixture of the methyl ester of formula

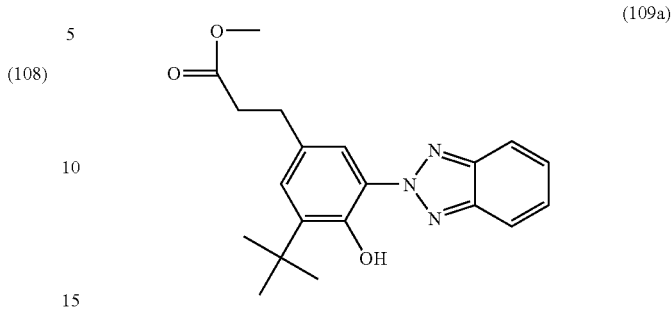

(109a)

(0.18 mol) and N,N'-diethylamino-propylamine (0.54 mol) is heated under reflux at 160–180° C. During the heating operation the reactor contents gradually form a readily stirrable melt. While passing nitrogen over the mixture, stirring is continued at 160° C. for from 16 to 20 hours, methanol being blown out via the reflux condenser. After changing over to distillation, the temperature is increased to 180° C. and the presssure is reduced to 10–30 mbar, the excess N,N'-diethylamino-propylamine being distilled off. After the final vacuum has been reached, stirring is continued for 1 h in order completely to remove amine residues. The amide of formula (101) is obtained in virtually quantitative yield and solidifies on cooling.

Alkylation

After the addition of methyl ethyl ketone (160 g) and water (160 g), dimethyl sulfate (0.189 mol) is added dropwise in the course of 30 min (20–25° C., pH 9.5±0.5). The mixture is subsequently heated to 60° C. and then stirred for 1 h. The reaction mixture is concentrated and the yield is determined by means of HPLC (the iodide of formula (103) described above is used as reference substance for the cation).

The yield is 90–100%.

Example 10

Preparation of the Compound of Formula

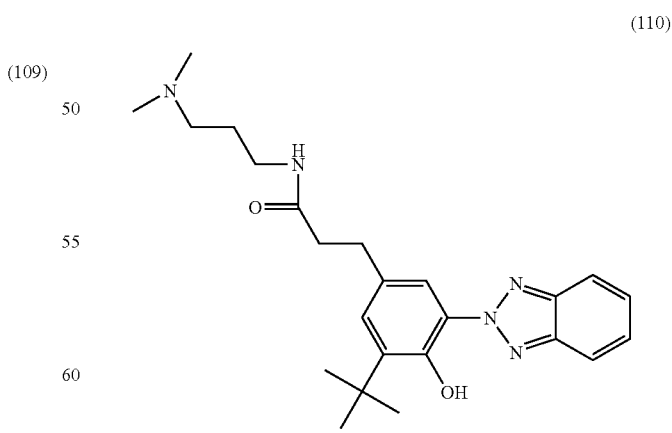

(110)

In accordance with the procedure described in Example 9 (amidation), the methyl ester of formula (109a) is reacted with N,N'-dimethylamino-propylamine. The yield of the compound of formula (110) is virtually quantitative.

NMR data:

$^{13}$C NMR (90 MHz, CDCl$_3$): δ=26.51 (CH$_2$), 29.94 (tert-butyl CH$_3$), 31.80 (CH$_2$), 35.86 (tert-butyl Cq), 39.28, 39.79 (CH$_2$CON, CONCH$_2$), 45.76 (CH$_3$N), 59.02 (CH$_2$N (CH$_3$)$_2$), 117.93 (aryl CH), 119.16 (aryl CH), 125.92 (aryl Cq), 127.98 (aryl CH), 128.53 (aryl CH), 132.05 (aryl Cq), 139.81 (aryl Cq), 143.00 (aryl Cq), 147.74 (aryl Cq), 172.27 (C=O).

Example 11

Preparation of the Compound of Formula

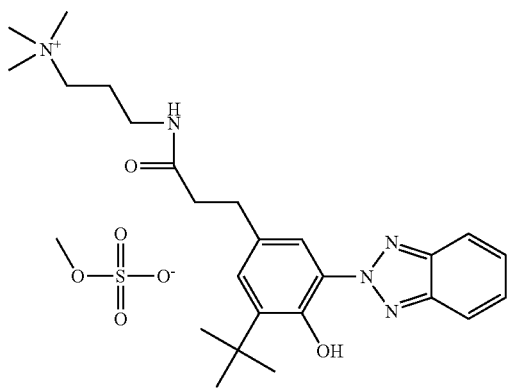

(111)

In accordance with the procedure described in Example 9 (alkylation), the compound of formula (110) is reacted with dimethyl sulfate. The yield is determined by means of HPLC and is 90–100% (The compound of formula (112) is used as reference for the cation).

Example 12

Preparation of the Compound of Formula

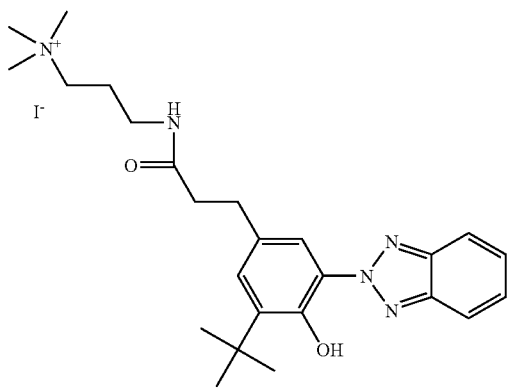

(112)

Analogously to the procedure described in Example 3, the target compound is prepared by reaction of the compound of formula (110) with methyl iodide.

NMR Data:

$^{13}$C NMR (90 MHz, [D$_6$]DMSO): δ=22.43 (CH$_2$), 28.83 (tert-butyl CH$_3$), 29.91 (CH$_2$), 34.53 (CH$_2$), 34.98 (tert-butyl Cq), 36.29 (CH$_2$), 39.72 (CH$_2$), 51.67 (CH$_3$N), 51.71 (CH$_3$N), 51.75 (CH$_3$N), 62.98 (CH$_2$N), 65.81 (CH$_2$N), 117.12 (aryl CH), 118.99 (aryl CH), 125.10 (aryl Cq), 127.56 (aryl CH), 131.65 (aryl Cq), 138.03 (aryl Cq), 142.0 (aryl Cq), 145.99 (aryl Cq), 171.01 (C=O).

Example 13

Preparation of the Compound of Formula

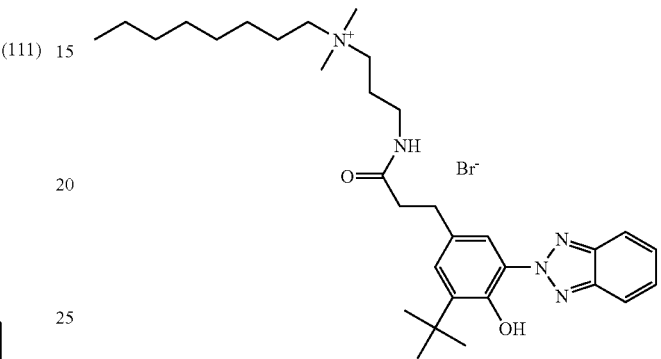

(113)

Analogously to the procedure described in Example 8, the target compound is prepared by reaction of the compound of formula (110) with 1-bromooctane.

NMR Data:

$^{13}$C NMR (90 MHz, CDCl$_3$): δ=14.39 (CH$_3$), 22.87 (CH$_2$), 23.07 (CH$_2$), 23.17 (CH$_2$), 26.52 (CH$_2$), 29.33 (CH$_2$), 29.40 (CH$_2$), 29.94 (CH$_3$), 31.55 (CH$_2$), 31.92 (CH$_2$), 35.85 (Cq), 36.52 (CH$_2$), 38.31 (CH$_2$), 51.26 (CH$_3$), 63.16 (CH$_2$), 65.12 (CH$_2$), 117.87 (aryl CH), 119.27 (aryl CH), 125.69 (aryl Cq), 128.02 (aryl CH), 128.77 (aryl CH), 132.19 (aryl Cq), 139.69 (aryl Cq), 142.93 (aryl Cq), 147.53 (aryl Cq), 173.64 (C=O).

Example 14

Preparation of the Compound of Formula

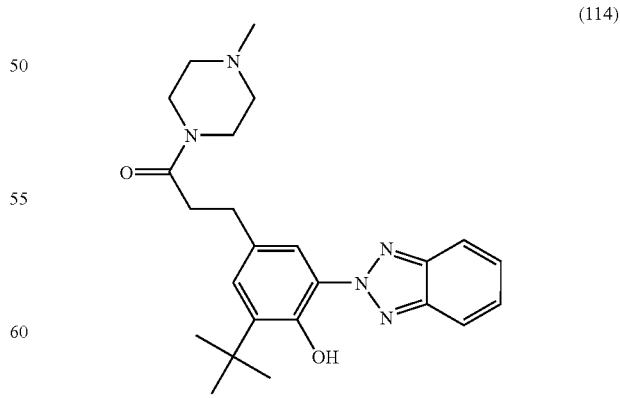

(114)

A mixture of toluene (5 g), triethylamine (0.85 g, 0.0084 mol) and 1-methylpiperazine (0.8 g, 0.008 mol) is slowly added dropwise at 0–5° C. to a solution of the carboxylic acid chloride of formula (101a) (3.0 g, 0.0084 mol) in toluene (35 g). Stirring is carried out for 15 h at room temperature. The reaction mixture is washed with $Na_2CO_3$ solution (5%) and water and the organic phase is dried. After removal of the solvent, light-yellow crystals are left behind.
Yield: 95%.

NMR Data:
$^{13}C$ NMR (90 MHz, $CDCl_3$): δ=29.97 (tert-butyl $CH_3$), 35.50 ($CH_2$), 35.89 (tert-butyl Cq), 42.00 ($CH_2$), 45.92 ($CH_2$), 46.39 ($CH_3N$), 55.12 ($CH_2$), 55.50 ($CH_2$), 117.95 (aryl CH), 119.25 (aryl CH), 128.58 (aryl CH), 128.61 (aryl CH), 132.14 (aryl Cq), 139.90 (aryl Cq), 143.04 (aryl Cq), 147.80 (aryl Cq), 170.94 (C=O).

Example 15

Demonstration of Substantivity 1 g of human hair is completely immersed in 10 ml of an aqueous solution (c=10 mmol/l)) of the UV absorber for 15 minutes. The extinction of the solution is determined by spectral photometry before and after the hair is immersed. The difference in the extinction values is used to calculate the amount of UV absorber taken up by 1 g of hair (mg of UV absorber per g of hair).

| UV absorber | mg of UV absorber per g of hair |
|---|---|
| compound of formula (108) | 25 (at pH 9.5; damaged hair*) |
|  | 9 (at pH 9.5; undamaged hair*) |
| compound of formula (109) | 31 (at pH 9.5; damaged hair) |
|  | 26 (at pH 5.5; damaged hair) |
|  | 3 (at pH 9.5; undamaged hair) |
|  | 2 (at pH 5.5; undamaged hair) |

*undamaged mid-blonde human hair or bleached human hair (damaged) is used

Example 16

Demonstration of the Antimicrobial Action for the Compound of Formula (108)

Determination of the Minimum Inhibitory Concentration (MIC Value) in Microtitre Plates Nutrient Medium:
casein-soybean flour-peptone bouillon for the preparation of the precultures of test bacteria and yeast.
Mycological slant agar for the preculture of moulds.

Test organisms:
S. *epidermidis* ATCC 12228
*Corynebacterium xerosis* ATCC 373
*Micrococcus luteus* ATCC 9341
*Enterococcus hirae* ATCC 10541
*Streptococcus mutans* ATCC 25175
*Klebsiella pneumoniae* ATCC 4352
*Salmonella choleraesuis* ATCC 9184
*Candida albicans* ATCC 10259
*P. ovale* ATCC 14521
*Epidermophyton floccosum* DSM 10709
*Trichophyton mentagrophytes* ATCC 9533
*Trichophyton rubrum* DSM 4167
*Trichoderma longibrachiatum* DSM 768

Procedure:
The test substances are predissolved in dimethyl sulfoxide (DMSO) and tested in a dilution series of 1:2.

The test organisms are cultured overnight in CASO bouillon and rinsed off with 10 ml of 0.85% sodium chloride solution (+0.1% TritonX-100).

The test organisms are adjusted to an organism count of $1–5\times10^6$ CFU/ml with 0.85% sodium chloride solution.

The test substances are prepipetted into microtitre plates in an amount of 8 μl per well.

Previously diluted organism suspensions are diluted 1:100 in CASO bouillon and added to the test substances in an amount of 192 μl per well.

The test batches are incubated for 48 hours at 37° C.

After incubation, the growth is determined by reference to the turbidity of the test batches (optical density) at 620 nm in a microplate reader.

The minimum inhibitory concentration (MIC value) is the concentration of substance at which (compared with the growth of the control) an appreciable inhibition of the growth ($\leq$20% growth) of the test organisms is ascertained.

One microtitre plate is used for each test organism and substance concentration. All substances are tested in duplicate.

The results are compiled in Table 2:

TABLE 2

| Microorganisms | MIC |
|---|---|
| S. *epidermidis* ATCC 12228 | 3.125 ppm |
| *Corynebacterium xerosis* ATCC 373 | 3.125 ppm |
| *Micrococcus luteus* ATCC 9341 | 3.125 ppm |
| *Enterococcus hirae* ATCC 10541 | *3.125 ppm |
| *Streptococcus mutans* ATCC 25175 | 3.125 ppm |
| *Klebsiella pneumoniae* ATCC 4352 | >100 ppm |
| *Salmonella choleraesuis* ATCC 9184 | >100 ppm |
| *Candida albicans* ATCC 10259 | 6.25 ppm |
| *P.ovale* ATCC 14521 | >25 ppm |
| *Epidermophyton floccosum* DSM 10709 | 12.5 ppm |
| *Trichophyton mentagrophytes* ATCC 9533 | 100 ppm |
| *Trichophyton rubrum* DSM 4167 | 25 ppm |
| *Trichoderma longibrachiatum* DSM 768 | 50 ppm |
| Growth ethanol control | ok |
| Growth control | ok |

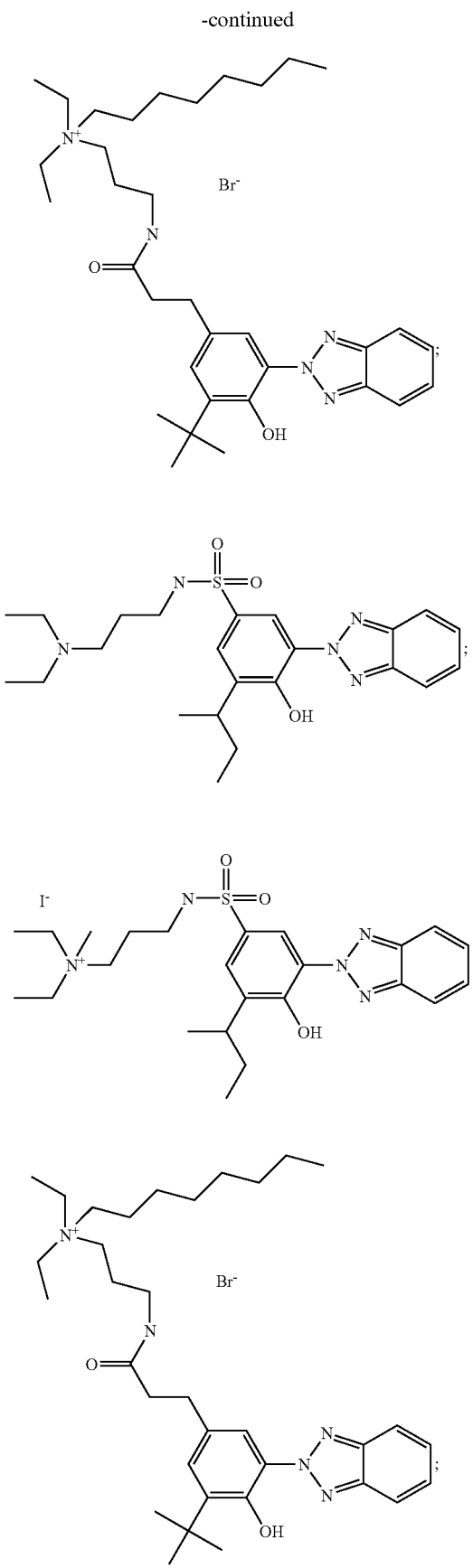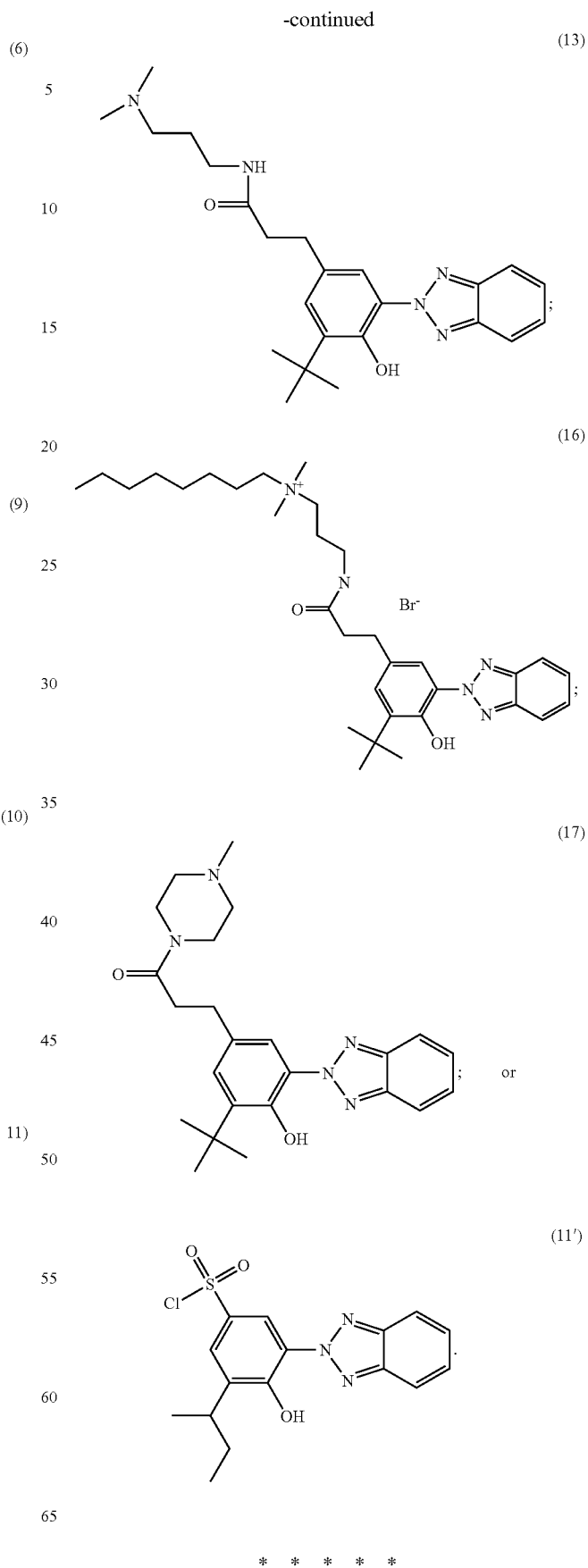

What is claimed is:
1. A compound of formula

(4)

[Chemical structure of compound of formula (4)]